US00PP27427P2

(12) United States Plant Patent
Pan

(10) Patent No.: US PP27,427 P2
(45) Date of Patent: Nov. 29, 2016

(54) ***LANTANA* PLANT NAMED 'LANZ0011'**

(50) Latin Name: *Lantana camara*
Varietal Denomination: LANZ0011

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,342

(22) Filed: Aug. 31, 2015

(51) Int. Cl.
*A01H 5/02* (2006.01)

(52) U.S. Cl.
USPC ..... Plt./227

(58) Field of Classification Search
USPC ..... Plt./227
CPC ..... A01H 5/02
See application file for complete search history.

*Primary Examiner* — Kent L Bell
(74) *Attorney, Agent, or Firm* — Joshua L. Price

(57) ABSTRACT

A new *Lantana* plant named 'LANZ0011', particularly distinguished by small size yellow flowers, excellent floriferousness, medium-spreading bushy habit, dark green foliage and early flowering.

1 Drawing Sheet

Latin name of the genus and species of the plant claimed: *Lantana camara.*

Varietal denomination: 'LANZ0011'.

BACKGROUND OF THE NEW PLANT

The present invention comprises a new *Lantana*, botanically known as *Lantana camara* and hereinafter referred to by the variety name 'LANZ0011'.

'LANZ0011' is a product of a planned breeding program. The new cultivar has small sized yellow flowers which are free flowering, excellent floriferousness, medium-spreading bushy habit, dark green foliage and early flowering.

'LANZ0011' originates from the cross-pollination between 680-1 and 709-3 made in July 2009 in a controlled breeding program in Gilroy, Calif., USA. The female parent has orange flowers, medium tall plant size and early bushy plant habit; the male parent has yellow flower, large flowers size, medium tall plant size and bushy plant habit.

The resulting seeds were sown in June 2010 in a greenhouse in Gilroy, Calif., USA. 'LANZ0011' was selected as one flowering plant within the progeny of the stated cross in November 2010.

The first act of asexual reproduction of 'LANZ0011' was accomplished when vegetative cuttings were propagated from the initial selection in December 2010 in a controlled environment in Gilroy, Calif.

BRIEF SUMMARY OF INVENTION

Horticultural examination of plants grown from cuttings of the plant initiated in spring of 2011 in Gilroy, Calif., and continuing thereafter, has demonstrated that the original combination of characteristics as herein disclosed for 'LANZ0011' are firmly fixed and are retained through successive generations of asexual reproduction.

'LANZ0011' has not been observed under all possible environmental conditions. The phenotype may vary significantly with variations in environment such as temperature, light intensity, and day length.

A Plant Breeder's Right for this cultivar has not yet been applied for.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0011' with colors being as true as possible with an illustration of this type.

Figure 1:
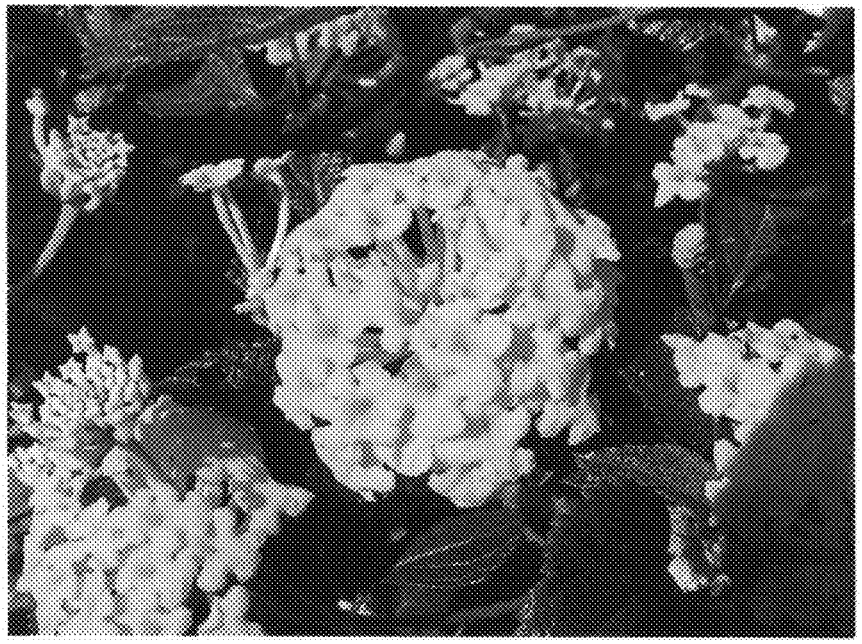
Figure 2:
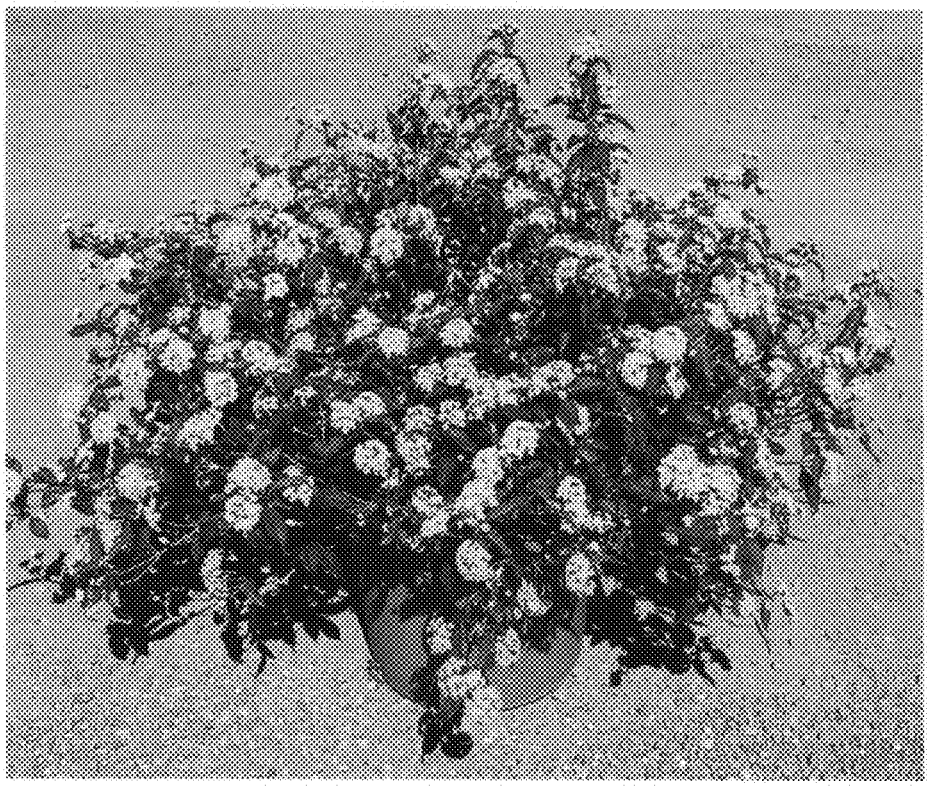

The photographic drawings show in FIG. 1, a close-up of the flowers, and in FIG. 2, a flowering potted plant of the new variety.

DETAILED BOTANICAL DESCRIPTION

The plant descriptions and measurements were taken in Gilroy, Calif. in August 2015. The plants were approximately 20 weeks old and were growing in 14 inch pots outdoors.

The aforementioned photographs were taken during August 2015 in Gilroy, Calif. The plants were growing in 14 inch pots outdoors. They were about 18 weeks of age.

TABLE 1

DIFFERENCES BETWEEN THE NEW VARIETY 'LANZ0011' AND A MOST SIMILAR VARIETY

| | 'LANZ0011' | 'BALUCYELL', U.S. Plant Pat. No. 14,684 |
|---|---|---|
| Overall flower color: | Yellow | Lighter flower color |
| Internode length: | 3.0-4.2 cm | Shorter 2.8-3.2 cm |
| Foliage size: | Smaller | Bigger |

Plant:

*Form, growth and habit.*—Semi-woody, grown as an annual or perennial; semi-spreading bushy habit; well branched.

*Plant height*.—30-35.0 cm.
*Plant height* (*inflorescence included*).—34-41.0 cm.
*Plant width*.—93-95.0 cm.

Foliage:
*Type*.—Opposite.
*Immature, leaf color, upper surface*.—Closest to RHS 139A.
*Lower surface*.—Closest to RHS 137A.
*Mature, leaf color, upper surface*.—Closest to RHS 147A.
*Lower surface*.—Closest to RHS 137A.
*Length*.—4.6-5.3 cm.
*Width*.—1.8-2.4 cm.
*Shape*.—Elliptic.
*Base shape*.—Rounded.
*Apex shape*.—Acute.
*Margin*.—Dentate.
*Texture, upper*.—Hirsute.
*Lower surface*.—Hirsute.
*Lower surface*.—RHS 137A.
*Pattern of veining*.—Pinnate.
*Petioles color*.—RHS 137C.
*Petioles length*.—0.4-0.7 cm.
*Diameter of petiole*.—0.1-0.15 cm.
*Texture* (*upper and lower surface*).—Hirsute with some very short glandular hairs.

Stem:
*Color of stem*.—RHS 137C.
*Length of stem*.—30-45.0 cm.
*Diameter*.—0.50 cm.
*Length of internodes*.—3.2-4.1 cm.
*Texture*.—Pilose, hirsute.

Inflorescence:
*Type*.—Umbel like, flattened semi-sphere the florets are sessile on an ovate receptacle.
*Blooming habit*.—Flowers continuously from spring through fall.
*Number of open flowers per inflorescence*.—45-50.
*Quantity of inflorescences per plant*.—About 200 (with open florets).
*Lastingness of individual blooms on the plant*.—About 4 weeks (depending on temperatures).
*Fragrance*.—Slightly spicy.
*Umbel horizontal diameter*.—About 3.3 cm.
*Umbel vertical height*.—1.7-2.0 cm.
*Peduncle color*.—RHS 137C.
*Length of peduncle*.—2.4-3.6 cm.
*Peduncle diameter*.—0.12 cm.
*Texture*.—Hirsute, glandular hairs.

Flower:
*Floret form*.—Corolla salver-shaped to shallow cup-shaped, with a relatively long tube at the base; each flower subtended by a single bract.
*Length of floret*.—1.0-1.3 cm.
*Width of floret*.—0.5-0.8 cm.
*Depth of floret*.—0.5-0.8 cm.
*Young floret, color upper surface*.—RHS 23B.
*Young floret, color lower surface*.—RHS 23C.
*Mature florets, color upper surface*.—RHS 21A outer part of petal and RHS 24A near throat.
*Mature floret, color lower surface*.—RHS 20A.
*Apex shape*.—Rounded.
*Degree of lobation*.—Moderate.
*Margin*.—Crenate.
*Base*.—Fused.
*Texture, upper surface*.—Papillose.
*Lower surface*.—Papillose.
*Tube, color outer surface*.—Closest to RHS 20B.
*Tube, color inner surface*.—Closest to RHS 21D.
*Tube, length*.—1.1 cm.
*Tube, diameter* (*at opening*).—0.11 cm.
*Tube, texture outer surface*.—Pubescent.
*Inner surface*.—Hirsute.

Bud (just before opening):
*Color*.—RHS 22A.
*Length*.—0.9-1.3 cm.
*Width*.—0.2-0.4 cm at the apex.
*Shape*.—Tubular with a flared apex.

Bract:
*Color*.—Closest to RHS 138B.
*Length*.—0.3-0.5 cm.
*Diameter*.—0.15-0.2 cm.
*Texture, upper surface*.—Hirsute.
*Lower surface*.—Hirsute.

Calyx:
*Number of sepals*.—5, fused sepals forming a short tube around the base of the floret.
*Color of sepals*.—RHS 147C.
*Length of sepals*.—0.25 cm.
*Width of sepals*.—0.15 cm.
*Apex shape*.—Acuminate.
*Margins*.—Entire.
*Texture, outer surface*.—Pubescent.
*Inner surface*.—Glabrous.

Reproductive organs:
*Gynoecium*.—Pistil quantity: One. Length: 0.4 cm. Style color: RHS 21D. Style length: 0.3 cm. Stigma color: RHS 147C. Ovary color: RHS 148C. Ovary length: 0.1 cm. Ovary diameter: 0.1 cm.
*Androecium*.—Stamen quantity:—4. Color of filaments: RHS 21D. Length filaments: 0.6-0.7 cm. Anther color: RHS 166B. Length of anthers: 0.1 cm. Color of pollen: RHS 10B. Pollen amount: Normal.
*Fertility/seed set*.—Has not been determined to date.
*Disease/pest resistance*.—Has not been determined to date.

What is claimed is:

1. A new and distinct variety of *Lantana* plant named 'LANZ0011,' substantially as illustrated and described herein.

* * * * *